(12) United States Patent
Nuss et al.

(10) Patent No.: US 8,487,117 B2
(45) Date of Patent: Jul. 16, 2013

(54) ATROPISOMERS OF (HYDROXYALKYL) PYRROLE DERIVATIVES

(75) Inventors: John Nuss, Danville, CA (US); Matthew Williams, San Mateo, CA (US); Raju Mohan, Encinitas, CA (US); Richard Martin, San Diego, CA (US); Tie-Lin Wang, San Diego, CA (US); Kazumasa Aoki, Tokyo (JP); Hiroyuki Tsuruoka, Tokyo (JP); Noriyuki Hayashi, Tokyo (JP); Tsuyoshi Homma, Tokyo (JP)

(73) Assignee: Exelixis, Inc., South San Francisco, CA (US)

( * ) Notice: Subject to any disclaimer, the term of this patent is extended or adjusted under 35 U.S.C. 154(b) by 50 days.

(21) Appl. No.: 13/122,147

(22) PCT Filed: Oct. 7, 2009

(86) PCT No.: PCT/US2009/059847
§ 371 (c)(1),
(2), (4) Date: Jul. 18, 2011

(87) PCT Pub. No.: WO2010/042622
PCT Pub. Date: Apr. 15, 2010

(65) Prior Publication Data
US 2011/0263673 A1 Oct. 27, 2011

Related U.S. Application Data

(60) Provisional application No. 61/103,715, filed on Oct. 8, 2008.

(51) Int. Cl.
*C07D 207/30* (2006.01)
*A61K 31/40* (2006.01)

(52) U.S. Cl.
USPC .......................................... 548/537; 514/423

(58) Field of Classification Search
USPC .......................................... 548/537; 514/423
See application file for complete search history.

(56) References Cited

FOREIGN PATENT DOCUMENTS

| WO | 2006/012642 A2 | 2/2006 |
| WO | 2008/126831 A1 | 10/2008 |

OTHER PUBLICATIONS

Silverman, R. B. (The Org. Chem. of Drug Design and Drug Action, Academic Press, Inc.: San Diego, 1992, pp. 4-51).*

* cited by examiner

*Primary Examiner* — Robert Havlin
(74) *Attorney, Agent, or Firm* — McDonnell Boehnen Hulbert & Berghoff LLP

(57) ABSTRACT

The present invention comprises a compound for the prevention and/or treatment of cardiovascular diseases. The compound is an atropisomer of a compound represented by the following general formula (I): wherein $R^1$ represents a C1-C3 alkyl group; $R^2$ represents a 2-hydroxy-C4-C6 alkyl group; $R^3$ represents a halogeno group, a halogeno-C1-C3 alkyl group and the like; $R^4$ represents a hydrogen atom, a halogeno group and the like; $R^5$ represents a C1-C3 alkyl group; and $R^6$ represents a hydrogen atom, a halogeno group and the like] or atropisomers thereof.

(I)

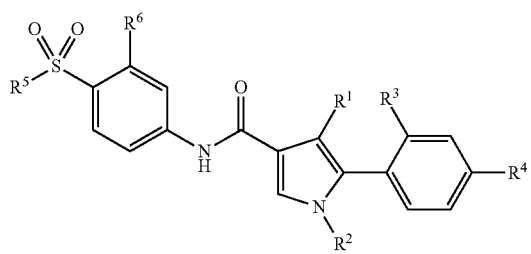

19 Claims, No Drawings

ATROPISOMERS OF (HYDROXYALKYL) PYRROLE DERIVATIVES

CROSS-REFERENCE TO RELATED APPLICATIONS

This application is a US national phase of International Application No. PCT/US2009/059847 filed on Oct. 7, 2009, which claims the benefit of U.S. Provisional Application No. 61/103,715 filed on Oct. 8, 2008, the disclosures of which are incorporated herein by reference in their entirety.

BACKGROUND OF THE INVENTION

1. Field of the Invention

The present invention relates to (hydroxyalkyl)pyrrole derivatives, atropisomers thereof, and to such compounds as preventive or therapeutic drugs and their uses for prevention or treatment of hypertension, angina pectoris, acute coronary syndrome, congestive heart failure, nephropathy, including diabetic nephropathy, arteriosclerosis, cerebral infarction, fibrosis and primary aldosteronism including such compounds, which have exceptional mineralocorticoid receptor antagonistic action.

2. Summary of the Related Art

Mineralocorticoid receptor (MR) (aldosterone receptor) is known to play an important role in controlling electrolyte balance in the body and blood pressure (for example, Advances in Physiology Education, 26(1): 8-20 (2002)), and mineralocorticoid receptor antagonist such as spironolactone and eplerenone having a steroid structure is known to be useful for treating hypertension and heart failure.

Hypertension is not only a primary cause of the development cardiovascular, cardiac and renal diseases, but a risk factor for the progression of these diseases initiated by other mechanisms such as atherosclerosis, cardiovascular disease, ischemic heart disease, diabetes, diabetic nephropathy, chronic glomerulonephritis and polycystic kidney disease (J. Am. Soc. Nephrol., 14:2395-2401 (2003)).

In renal failure, as with the case of chronic heart failure, a number of clinical trials have established that interruption of the RAAS cascade with ACE inhibitors is beneficial in limiting renal disease (Am. J. Kid. Dis., 37 (4): 677-688 (2001). Additional studies have also established that aldosterone antagonists can attenuate proteinuria and renal damage typically observed in progressive renal disease and offer further therapeutic benefit compared to ACE inhibitors alone (Hypertension., 31:451-458 (1998)).

Here, as a mineralocorticoid receptor antagonist having a non-steroidal skeleton, pyrrole derivatives described in pamphlet of International Publication No. WO 2006/012642 have been known; however, atropisomers of a compound represented by the general formula (I) of the present invention have not been known.

SUMMARY OF THE INVENTION

As a result of conducting extensive studies on the pharmacological activity of various (hydroxyalkyl)pyrrole derivatives with the intention to develop a superior preventive drug or a therapeutic drug for cardiovascular disease, the present inventors have found that there are atropisomers regarding a compound represented by the general formula (I), and that one of the atropisomers is extremely superior in sustention of mineralocorticoid receptor antagonistic action (in vitro activity and in vivo activity) and drug efficacy compared to the other. Furthermore, it was found that one atropisomer has superior properties in terms of solubility, oral absorbability, blood concentration, metabolic stability and safety and the like, and that it is useful as a medicament, preferably as a preventive drug or a therapeutic drug (especially a therapeutic drug), for diseases such as hypertension, angina pectoris, acute coronary syndrome, congestive heart failure, nephropathy, including diabetic nephropathy, arteriosclerosis, cerebral infarction, fibrosis, primary aldosteronism or heart disease, more preferably for congestive heart failure, nephropathy, including diabetic nephropathy, hypertension and the like, particularly preferably for hypertension, and particularly preferably for diabetic nephropathy, thereby completing the invention.

DETAILED DESCRIPTION OF THE INVENTION

The present invention provides a compound represented by the general formula (I) (including an atropisomer thereof), pharmaceutical compositions thereof (including a medicament as a preventive or therapeutic drug (especially a therapeutic drug)) and their use for the prevention or treatment of hypertension, angina pectoris, acute coronary syndrome, congestive heart failure, nephropathy, including diabetic nephropathy, arteriosclerosis, cerebral infarction, fibrosis, primary aldosteronism or heart disease (more preferably for congestive heart failure, nephropathy, including diabetic nephropathy, and hypertension; particularly preferably for hypertension), which have a excellent mineralocorticoid receptor antagonistic action. Preferred compounds/compositions comprise the atropisomer of the compound of the invention having superior mineralocorticoid receptor antagonist activity compared to the other atropisomer(s) of that structure.

That is, the present invention provides (1): a compound represented by the following general formula (I):

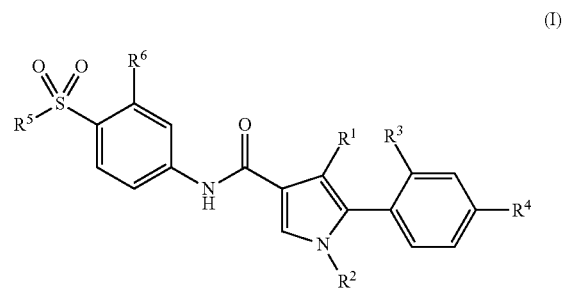

an N-oxide thereof; a diastereomer, racemate, or compound enriched in a diastereomer thereof; an atropisomer, equal mixtures of atropisomers, or a compound enriched in an atropisomer of the foregoing; or a pharmaceutically acceptable salt of the foregoing, wherein, $R^1$ represents a C1-C3 alkyl group;

$R^2$ represents a 2-hydroxy-C4-C6 alkyl group;

$R^3$ represents a halogeno group, a C1-C3 alkyl group, a C1-C3 alkoxy group, a halogeno-C1-C3 alkyl group or a halogeno-C1-C3 alkoxy group;

$R^4$ represents a hydrogen atom, a halogeno group or a C1-C3 alkyl group;

$R^5$ represents a C1-C3 alkyl group; and $R^6$ represents a hydrogen atom, a halogeno group, a C1-C3 alkyl group or a C1-C3 alkoxy group.

In addition, the present invention comprises the following (2): atropisomers of a compound represented by the general formula (I);

(3): the compound according to the aforementioned (1) or (2), wherein $R^1$ is a methyl group;

(4): the compound according to any one of the aforementioned (1) through (3), wherein $R^2$ is a 2-hydroxy-1-methylpropyl group;

(5): the compound according to any one of the aforementioned (1) through (3), wherein $R^2$ is a (1R,2S)-2-hydroxy-1-methylpropyl group;

(6): the compound according to any one of the aforementioned (1) through (5), wherein $R^3$ is a methyl group, a chloro group, a halogenomethyl group or a halogenomethoxy group;

(7): the compound according to any one of the aforementioned (1) through (5), wherein $R^3$ is a chloro group, a difluoromethyl group, a trifluoromethyl group, a difluoromethoxy group or a trifluoromethoxy group;

(8): the compound according to any one of the aforementioned (1) through (5), wherein $R^3$ is a chloro group or a trifluoromethyl group;

(9): the compound according to any one of the aforementioned (1) through (8), wherein $R^4$ is a hydrogen atom or a halogeno group;

(10): the compound according to any one of the aforementioned (1) through (8), wherein $R^4$ is a hydrogen atom, a fluoro group or a chloro group;

(11): the compound according to any one of the aforementioned (1) through (10), wherein $R^5$ is a methyl group;

(12): the compound according to any one of the aforementioned (1) through (11), wherein $R^6$ is a hydrogen atom, a chloro group or a methyl group; and (13): the compound according to any one of the aforementioned (1) through (11), wherein $R^6$ is a hydrogen atom.

Furthermore, the present invention provides (14): the following compounds:

1-[2-hydroxy-1-methylpropyl]-4-methyl-N-[4-(methylsulfonyl)phenyl]-5-[2-(trifluoromethyl)phenyl]-1H-pyrrole-3-carboxamide;

5-[4-fluoro-2-(trifluoromethyl)phenyl]-1-[2-hydroxy-1-methylpropyl]-4-methyl-N-[4-(methylsulfonyl)phenyl]-1H-pyrrole-3-carboxamide;

5-[4-chloro-2-(trifluoromethyl)phenyl]-1-[2-hydroxy-1-methylpropyl]-4-methyl-N-[4-(methylsulfonyl)phenyl]-1H-pyrrole-3-carboxamide;

and 5-(2-chloro-4-fluorophenyl)-1-[2-hydroxy-1-methylpropyl]-4-methyl-N-[4-(methylsulfonyl)phenyl]-1H-pyrrole-3-carboxamide;

and N-oxides, atropisomers of any the foregoing, and pharmaceutically acceptable salts of any of the foregoing.

In addition, the present invention provides (15): the following compounds:

1-[(1R,2S)-2-hydroxy-1-methylpropyl]-4-methyl-N-[4-(methylsulfonyl)phenyl]-5-[2-(trifluoromethyl)phenyl]-1H-pyrrole-3-carboxamide;

5-[4-fluoro-2-(trifluoromethyl)phenyl]-1-[(1R,2S)-2-hydroxy-1-methylpropyl]-4-methyl-N-[4-(methylsulfonyl)phenyl]-1H-pyrrole-3-carboxamide;

5-[4-chloro-2-(trifluoromethyl)phenyl]-1-[(1R,2S)-2-hydroxy-1-methylpropyl]-4-methyl-N-[4-(methylsulfonyl)phenyl]-1H-pyrrole-3-carboxamide;

5-(2-chloro-4-fluorophenyl)-1-[(1R,2S)-2-hydroxy-1-methylpropyl]-4-methyl-N-[4-(methylsulfonyl)phenyl]-1H-pyrrole-3-carboxamide;

and N-oxides, atropisomers of any the foregoing, and pharmaceutically acceptable salts of any of the foregoing.

Further, the present invention provides (16): one of the atropisomers of the compound according to any one of the aforementioned (1) through (15) which shows greater mineralocorticoid receptor antagonist activity compared to the other atropisomer(s).

In addition, the present invention provides (17): a medicament comprising the atropisomer according to any one of the aforementioned (1) through (16) as an active ingredient;

(18): a preventive drug or a therapeutic drug for a cardiovascular disease, comprising the atropisomer according to any one of the aforementioned (1) through (16) as an active ingredient;

(19): a preventive drug or a therapeutic drug for hypertension, comprising the atropisomer according to any one of the aforementioned (1) through (16) as an active ingredient; and (20): a preventive drug or a therapeutic drug for diabetic nephropathy, comprising the atropisomer according to any one of the aforementioned (1) through (16) as an active ingredient.

Furthermore, the present invention provides (21): a pharmaceutical composition comprising the atropisomer according to any one of the aforementioned (1) through (16) and a pharmacologically/pharmaceutically acceptable carrier.

Because one of the atropisomers of (hydroxyalkyl)pyrrole derivatives of the present invention has stronger mineralocorticoid receptor antagonist activity compared to the other(s), it is useful as a preventive drug or a therapeutic drug (especially a therapeutic drug) for prevention or treatment of diseases such as hypertension, angina pectoris, acute coronary syndrome, congestive heart failure, nephropathy, including diabetic nephropathy, arteriosclerosis, cerebral infarction, fibrosis, primary aldosteronism or heart disease, more preferably for congestive heart failure, nephropathy, including diabetic nephropathy, hypertension and the like, particularly preferably for hypertension, and particularly preferably diabetic nephropathy.

The atropisomers of a compound represented by the general formula (I) of the present invention have a superior mineralocorticoid receptor antagonist activity relative to the other atropisomer(s) having the same structure, show high oral absorbability, plasma concentration levels, and long half-life in the blood, and showed superior pharmacological activity. In addition, such atropisomers of a compound represented by the general formula (I) of the present invention have superior internal kinetics/pharmacokinetics such as body distribution, half-life in blood and the like, and have low toxicity regarding organs such as kidney and liver. Furthermore, the atropisomers of a compound represented by the general formula (I) of the present invention are extremely stable; for example, no racemization was observed after letting it stand in methanol at room temperature for 7 days, and in an acetonitrile-phthalic acid buffer at 60° C. for 4 hours.

Therefore, the atropisomers of the compound represented by the general formula (I) of the present invention are, for example, useful as a medicament, and are useful particularly as a medicament to prevent or treat various cardiovascular diseases (preferably hypertension, angina pectoris, acute coronary syndrome, congestive heart failure, nephropathy, including diabetic nephropathy, arteriosclerosis, cerebral infarction, fibrosis, primary aldosteronism or heart disease).

DEFINITIONS

Substituents in the present specification will be explained hereinafter.

(1) A "halogeno group" is a fluoro group, a chloro group and a bromo group, and preferably a fluoro group and a chloro group.

(2) A "C1-C3 alkyl group" is a linear or branched alkyl group having 1 to 3 carbon atoms such as a methyl group, an ethyl group, a n-propyl group and an isopropyl group, preferably a methyl group and an ethyl group.

(3) A "C1-C3 alkoxy group" is a C1-C3 alkyloxy group structured from the aforementioned "C1-C3 alkyl group", and represents for example, a linear or branched alkoxy group having 1 to 3 carbon atoms such as a methoxy group, an ethoxy group, a n-propoxy group and an isopropoxy group, and preferably represents a methoxy group.

(4) A "2-hydroxy-C4-C6 alkyl group" is a group in which a linear or branched "C4-C6 alkyl group" substituted with one hydroxy group at the 2-position, and there can be mentioned for example, a 2-hydroxy-1-methylpropyl group, a 2-hydroxy-2-methylpropyl group, a 2-hydroxybutyl group, a 2-ethyl-2-hydroxybutyl group, a 1-ethyl-2-hydroxybutyl group, a 2-hydroxy-(3-methyl)butyl group, a 2-hydroxy-(3,3-dimethyl)butyl group, a 2-hydroxypentyl group and a 2-hydroxyhexyl group, preferably a 2-hydroxy-1-methylpropyl group.

(5) A "halogeno-C1-C3 alkyl group" is a group in which the aforementioned "C1-C3 alkyl group" is substituted with the same or different 1 to 5 halogeno groups, and there can be mentioned for example, a fluoromethyl group, a difluoromethyl group, a trifluoromethyl group, a chlorodifluoromethyl group, a 2-fluoroethyl group, a 2-fluoro-1-methylethyl group, a 2,2,2-trifluoroethyl group, a 1,1,2,2,2-pentafluoroethyl group and a 3-fluoropropyl group, preferably a difluoromethyl group, a trifluoromethyl group, a 2-fluoroethyl group, a 2-fluoropropyl group and a 2-fluoro-1-methylethyl group and the like.

(6) A "halogeno-C1-C3 alkoxy group" is a group in which the aforementioned "C1-C3 alkoxy group" is substituted with the same or different 1 to 5 halogeno groups, and there can be mentioned for example, a fluoromethoxy group, a difluoromethoxy group, a trifluoromethoxy group, a 2-fluoroethoxy group, a 1,1-difluoroethoxy group, a 1,1,2,2,2-pentafluoroethoxy group and a 3-fluoropropoxy group, preferably a difluoromethoxy group, a trifluoromethoxy group and the like.

Hereinafter, the present invention will be explained in detail.

$R^1$, $R^2$, $R^3$, $R^4$, $R^5$ and $R^6$ in the general formula (I) will be explained.

(I)

$R^1$ in the general formula (I) represents:
(a) C1-C3 alkyl;
(b) methyl or ethyl; or
(c) methyl.

$R^2$ in the general formula (I) represents:
(a) 2-hydroxy-C4-C6 alkyl;
(b) 2-hydroxy-1-methylpropyl; or
(c) (1R,2S)-2-hydroxy-1-methylpropyl.

$R^3$ in the general formula (I) represents:
(a) halogeno, C1-C3 alkyl, C1-C3 alkoxy, halogeno-C1-C3 alkyl, or a halogeno-C1-C3 alkoxy; as the halogeno group, a chloro group is preferable; as the C1-C3 alkyl group, a methyl group is preferable; as the C1-C3 alkoxy group, a methoxy group is preferable; as the halogeno-C1-C3 alkyl group, a difluoromethyl group or a trifluoromethyl group is preferable; as the halogeno-C1-C3 alkoxy group, a difluoromethoxy group or a trifluoromethoxy group is preferable;
(b) methyl, chloro, halogenomethyl, or halogenomethoxy;
(c) chloro, difluoromethyl, trifluoromethyl, difluoromethoxy, or trifluoromethoxy; or
(d) chloro or trifluoromethyl.

$R^4$ in the general formula (I) represents:
(a) hydrogen, halogeno, or C1-C3 alkyl; or
(b) hydrogen or halogeno.

$R^5$ in the general formula (I) represents:
(a) C1-C3 alkyl; or
(b) methyl.

$R^6$ in the general formula (I) represents:
(a) hydrogen, halogeno, C1-C3 alkyl, or C1-C3 alkoxy;
(b) hydrogen, chloro, or methyl; or
(c) hydrogen.

As a preferable compound represented by the general formula (I), there can be mentioned one compound selected from the group consisting of the following:

1-[2-hydroxy-1-methylpropyl]-4-methyl-N-[4-(methylsulfonyl)phenyl]-5-[2-(trifluoromethyl)phenyl]-1H-pyrrole-3-carboxamide;

5-[4-fluoro-2-(trifluoromethyl)phenyl]-1-[2-hydroxy-1-methylpropyl]-4-methyl-N-[4-(methylsulfonyl)phenyl]-1H-pyrrole-3-carboxamide;

5-[4-chloro-2-(trifluoromethyl)phenyl]-1-[2-hydroxy-1-methylpropyl]-4-methyl-N-[4-(methylsulfonyl)phenyl]-1H-pyrrole-3-carboxamide;

5-(2-chloro-4-fluorophenyl)-1-[2-hydroxy-1-methylpropyl]-4-methyl-N-[4-(methylsulfonyl)phenyl]-1H-pyrrole-3-carboxamide;

or an N-oxide, atropisomer of any of the foregoing, or a pharmaceutically acceptable salt of any of the foregoing. Among a pair of atropisomers of the four stereoisomers of any of the foregoing, the one which shows a stronger mineralocorticoid receptor antagonistic action is more preferable.

Preferable compounds represented by the general formula (I) include (Table 1):

TABLE 1

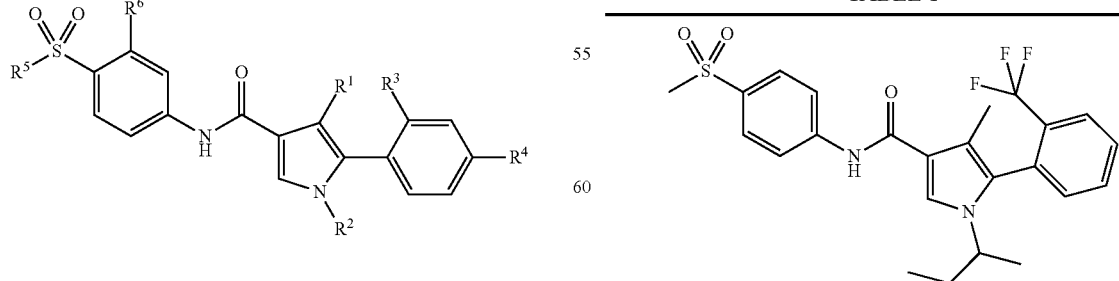

TABLE 1-continued

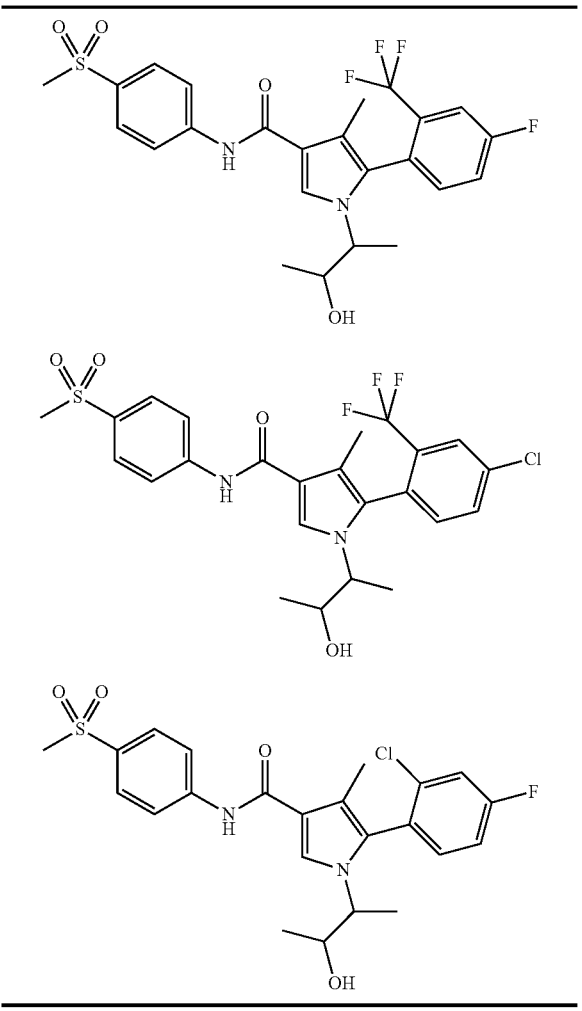

an N-oxide, atropisomer of any of the foregoing, and a pharmaceutically acceptable salt of any of the foregoing. Among a pair of atropisomers of the four stereoisomers of any of the foregoing, the one which shows a stronger mineralocorticoid receptor antagonistic action is more preferable.

Further, as a preferable compound represented by the general formula (I), are the following:

1-[(1R,2S)-2-hydroxy-1-methylpropyl]-4-methyl-N-[4-(methylsulfonyl)phenyl]-5-[2-(trifluoromethyl)phenyl]-1H-pyrrole-3-carboxamide;

5-[4-fluoro-2-(trifluoromethyl)phenyl]-1-[(1R,2S)-2-hydroxy-1-methylpropyl]-4-methyl-N-[4-(methylsulfonyl)phenyl]-1H-pyrrole-3-carboxamide;

5-[4-chloro-2-(trifluoromethyl)phenyl]-1-[(1R,2S)-2-hydroxy-1-methylpropyl]-4-methyl-N-[4-(methylsulfonyl)phenyl]-1H-pyrrole-3-carboxamide;

5-(2-chloro-4-fluorophenyl)-1-[(1R,2S)-2-hydroxy-1-methylpropyl]-4-methyl-N-[4-(methylsulfonyl)phenyl]-1H-pyrrole-3-carboxamide;

an N-oxide, atropisomers of any of the foregoing, and pharmaceutically acceptable salts of any of the foregoing. Among the atropisomers, the one which shows a stronger mineralocorticoid receptor antagonist activity is more preferable.

Preferable compounds represented by the general formula (I) include (Table 2):

TABLE 2

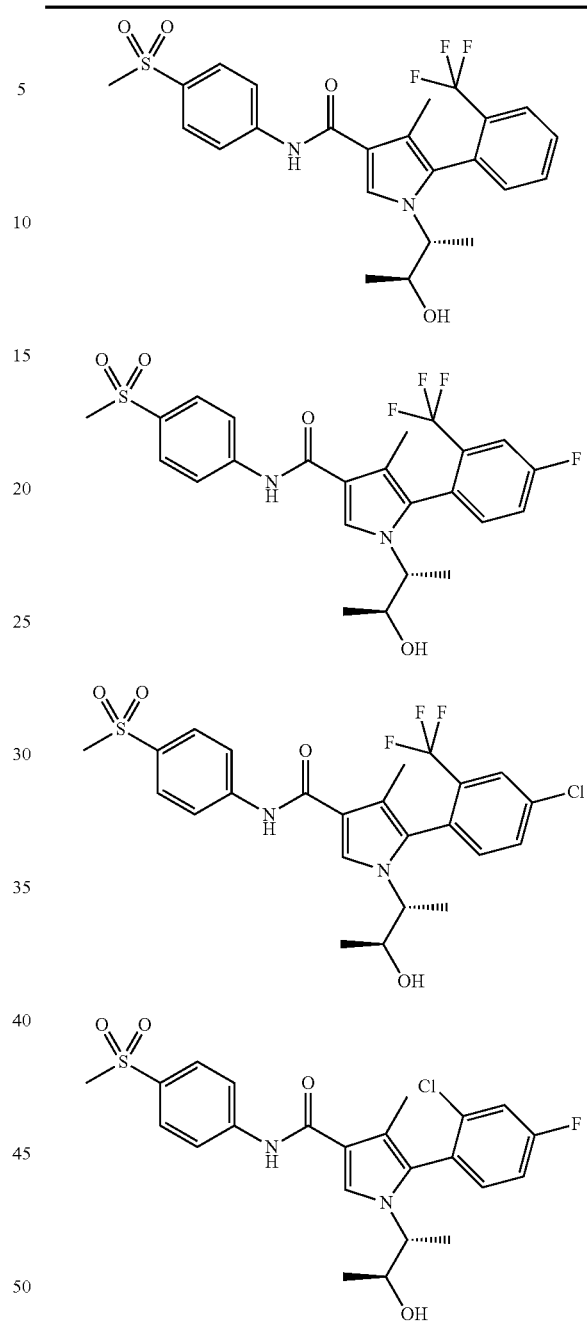

N-oxides thereof, atropisomers of any of the foregoing, and pharmaceutically acceptable salts of any of the foregoing. Among the atropisomers, the one which shows a stronger mineralocorticoid receptor antagonist activity is more preferable.

Here, "congestive heart failure" in the present specification includes "chronic cardiac failure" and "CHF (chronic heart failure)".

Specific examples of "fibrosis" in the present specification include endocardial fibrosis, vascular fibrosis, kidney fibrosis and hepatic fibrosis.

The term "heart disease" in the present specification means ischemic heart disease, heart failure, heart systolic dysfunction, cardiac dilatation dysfunction, myocardial necrosis, pulmonary venous congestion, atrial fibrillation, myocardial infarction, myocardial fibrosis or chronic heart failure.

The terms "renal disease" or "kidney disease" or "nephropathy" in the present specification include diabetic nephropathy, chronic glomerulonephritis, polycystic kidney, non-diabetic nephropathy and chronic renal disease.

Hereinafter, the production process for the compound represented by the formula (I) of the present invention will be explained.

The compound of formula (I) of the present invention can be produced by the method shown in the following [Scheme 1].

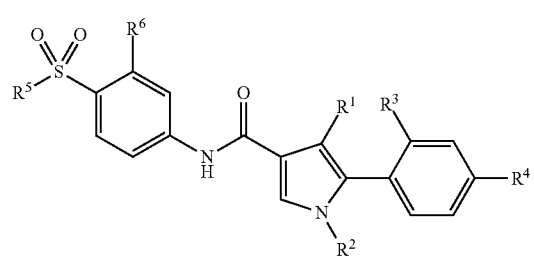

The compound of formula (I) can be produced by the method shown in the following [Scheme 1].

The compound of formula (I) can be produced by first preparing a 5-arylpyrrolecarboxylic acid ester derivative (3) via a coupling reaction of 5-bromopyrrole (1) and compound (2) which is an arylboronic acid derivative, followed by hydrolysis of the compound (3). Then, compound (5) which is an acid chloride is prepared and a condensation reaction of compound (5) and aniline (6) is carried out to give compound (7) which is an amide derivative, followed by alkylation of compound (7).

In a case where the compound of formula (I) has optical isomers stemming from an asymmetric carbon, axial asymmetry and the like, a single isomer can be obtained by carrying out an optical resolution as necessary.

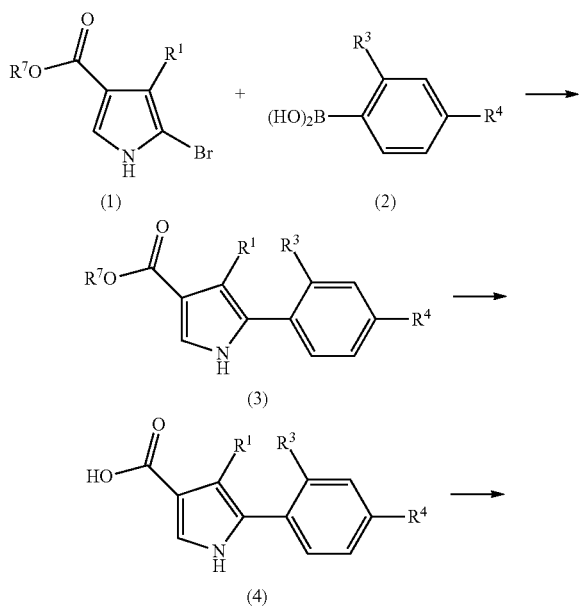

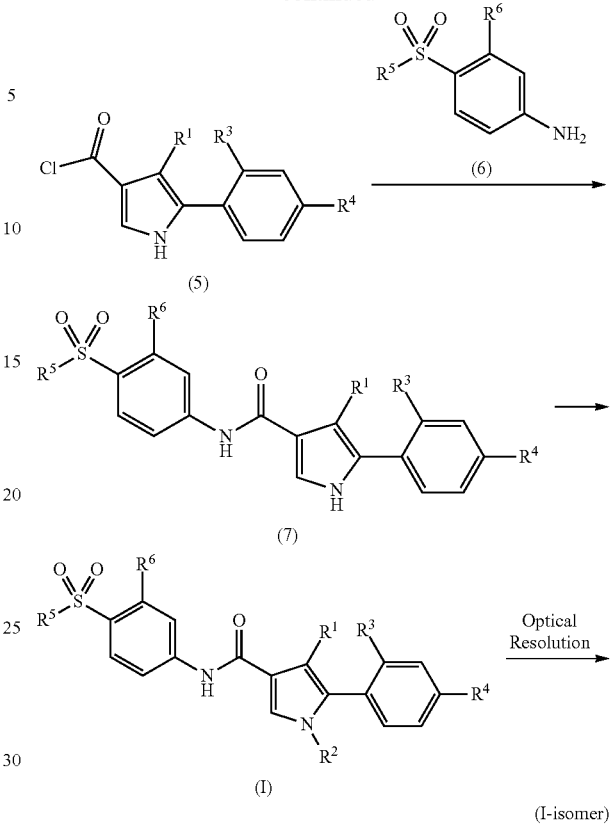

(In the aforementioned formulas, $R^1$ represents a C1-C3 alkyl group; $R^2$ represents a 2-hydroxy-C4-C6 alkyl group; $R^3$ represents a halogeno group, a C1-C3 alkyl group, a C1-C3 alkoxy group, a halogeno-C1-C3 alkyl group or a halogeno-C1-C3 alkoxy group; $R^4$ represents a hydrogen atom, a halogeno group or a C1-C3 alkyl group; $R^5$ represents a C1-C3 alkyl group; $R^6$ represents a hydrogen atom, a halogeno group, a C1-C3 alkyl group or a C1-C3 alkoxy group; and $R^7$ represents a C1-C4 alkyl group or an aryl group.)

As a reference document for the coupling reaction (cross-coupling reaction) of the compound (1) which is a bromopyrrole derivative and the arylboronic acid derivative (2), patent document (WO 2006/012642) can be mentioned. As a catalyst for the coupling reaction, a general palladium reagent can be used, and tetrakis(triphenylphosphine)palladium (0) is preferable. As a base, sodium carbonate, potassium carbonate, sodium hydrogencarbonate, sodium hydroxide and the like can be used, and sodium carbonate is preferable. As a reaction solvent, water or a halogenated hydrocarbon solvents such as methylene chloride, hydrocarbon solvents such as toluene, ether solvents such as tetrahydrofuran, inert polar solvents such as N,N-dimethylformamide and N,N-dimethylacetamide or the like can be used alone or as a solvent mixture, and a solvent mixture of toluene and water and the like is preferable. As the reaction temperature, it is in the range of 0° C. to boiling point of the solvent, preferably in the range of room temperature to boiling point of the solvent. As the reaction time, it is usually from about 0.5 to about 24 hours.

In the alkaline hydrolysis of compound (3) which is a pyrrolecarboxylic acid ester derivative, and in the condensation reaction of compound (5), which is a pyrrolecarboxylic acid chloride derivative obtained by the halogenation reaction following the hydrolysis, with compound (6) which is an aniline derivative or with a salt thereof, methods described in patent document (WO 2006/012642) shall be used. First, in the conversion reaction to give the acid chloride of pyrrolecarboxylic acid (4), a general halogenating reagent can be used, and is preferably oxalyl chloride. In the condensation reaction of compound (5) and compound (6) which is an aniline derivative, it is preferable to carryout the reaction in the presence of a base. As the base, an organic base such as triethylamine and diisopropylethylamine are preferable. As a solvent for the condensation reaction, halogenated hydrocarbon solvents such as methylene chloride, hydrocarbon solvents such as toluene, ether solvents such as tetrahydrofuran or polar solvents such as N,N-dimethylformamide and N,N-dimethylacetamide are preferable. As the reaction temperature, it is in the range of −20° C. to boiling point of the solvent, preferably in the range of room temperature to boiling point of the solvent. As the reaction time, it is usually from about 2 to about 24 hours.

In the alkylation of compound (7) which is an amide derivative of pyrrolecarboxylic acid, a known alkylation method which is carried out under a basic condition may be used. As an alkylating reagent, for example, cyclic sulfuric acid ester derivatives such as 4,5-dimethyl-1,3,2-dioxathiolane 2,2-dioxide, carbonic acid ester derivatives and the like can be used, and is preferably (4S,5S)-4,5-dimethyl-1,3,2-dioxathiolane 2,2-dioxide [reference literature: Bull. Chem. Soc. Jpn. 66, 513-522 (1993)]. As a base, sodium tert-butoxide, sodium hydride, potassium carbonate and the like can be used, and is preferably sodium tert-butoxide. As a reaction solvent, alcohol solvents such as ethanol, halogenated hydrocarbon solvents such as methylene chloride, hydrocarbon solvents such as toluene, ether solvents such as tetrahydrofuran, and polar solvents such as N,N-dimethylformamide and N,N-dimethylacetamide can be used, and is preferably N,N-dimethylacetamide. As the reaction temperature, it is in the range of −20° C. to boiling point of the solvent, preferably in the range of room temperature to boiling point of the solvent. As the reaction time, it is usually from about 0.5 to about 24 hours.

[Scheme 2]

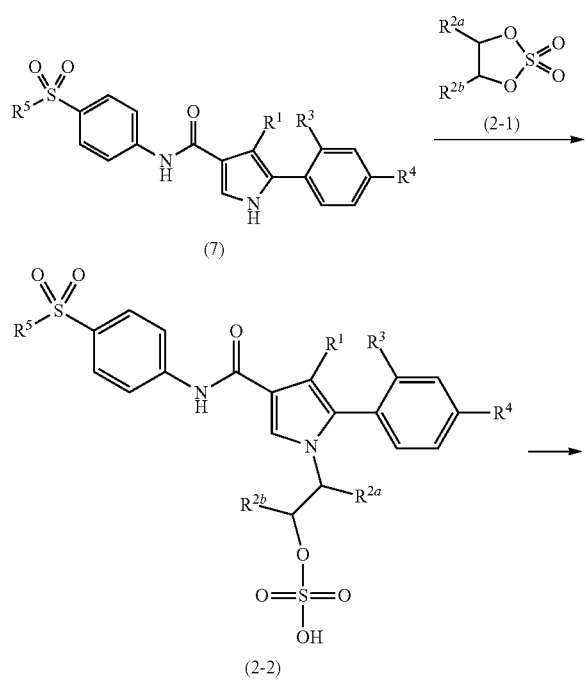

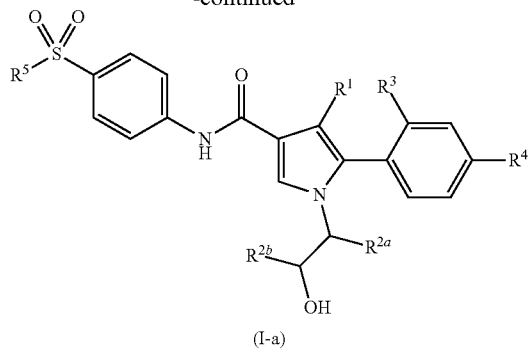

(I-a)

(Here, $R^{2a}$ and $R^{2b}$ are:
1) the same or different from each other, and represent a methyl group or an ethyl group, or 2) either one of $R^{2a}$ or $R^{2b}$ is a hydrogen atom, and the other represents a methyl group, an ethyl group, a propyl group, an isopropyl group, a butyl group or a tert-butyl group; and $R^1$, $R^3$, $R^4$, $R^5$ and $R^6$ represent the same as described above.)

Compound of formula (I-a), which is an alcohol derivative, can be produced as described in [Scheme 2], by first preparing compound (2-2), which is a sulfuric ester derivative, in the presence of an acid catalyst by using as an alkylating agent a cyclic sulfuric acid ester derivative (2-1) which is commercially available or can be synthesized by a known method, and then hydrolyzing the compound (2-2). As the acid catalyst, hydrochloric acid, sulfuric acid, acetic acid and the like can be used, and is preferably hydrochloric acid. As a solvent, water, alcohol solvents such as ethanol, halogenated hydrocarbon solvents such as methylene chloride, inert hydrocarbon solvents such as toluene, inert ether solvents such as tetrahydrofuran, or inert polar solvents such as N,N-dimethylformamide and the like can be used, and is preferably tetrahydrofuran. As the reaction temperature, it is in the range of 0° C. to boiling point of the solvent, preferably in the range of room temperature to boiling point of the solvent. As the reaction time, it is usually from about 0.5 to about 24 hours.

With respect to the aforementioned compound (I), there are cases where there exist atropisomers stemming from axial asymmetry between pyrrole and phenyl, or optical isomers stemming from sp3 asymmetric carbon or the like. Optical resolution of atropisomers is essentially the same as that of enantiomers stemming from sp3 asymmetric carbon or the like. For example, direct resolution can be carried out by high performance liquid chromatography using a chiral column. As the chiral column, there can be mentioned for example, CHIRALPAK AD-H, AS-H and the like.

The atropisomers in the present invention are structural isomers based on axial or facial chirality, arising from constrained intramolecular rotation. The compound having the general formula (I) of the present invention has two atropisomers that stem from axial asymmetry which arises from restriction of the rotation of the bond connecting the phenyl group having $R^3$ group as a substituent and the substituted pyrrole ring, due to steric hindrance. With respect to the atropisomers of the present invention, in a case where the compound having the general formula (I) or the compound of the general formula (I) has isomers arising from an asymmetric carbon and the like, it means either one of a pair of atropisomers that exist for each of such isomeric compounds. The atropisomer which with superior pharmacological/pharmacokinetic activity, stability, internal kinetics, safety and the like, and has preferable properties as a medicament is preferred.

Here, the present invention comprises, among the atropisomers existing for the compound of the general formula (I), the atropisomer having superior or preferred pharmacological and/or pharmacokinetic activity, stability, internal kinetics, safety and the like, and has preferable properties as a medicament; however, the present invention also comprises compounds/compositions enriched in the atropisomer having the preferable properties as a major component, or also includes a mixture with the other atropisomer at any ratio, so long as it demonstrates such preferable properties. In compounds/compositions enriched in the atropisomer having superior and/or preferred properties, the atropisomer having such properties is present in greater concentration than the other atropisomer(s). Preferably, the preferred atropisomer comprises greater than 50%, 60%, 70%, 80%, 90%, 95%, 98%, or 99% of the atropisomers of the same structure. In a preferred embodiment, atropisomers of the same structure other than the preferred atropisomer are undetectable.

As separation and purification methods for the atropisomers produced by the aforementioned methods include, for example, chromatography, although the method is not limited to such. Hereinafter, details of a general optical resolution method using chromatography will be described.

In the optical resolution method using chromatography, when a stationary phase which incorporates an asymmetric element bonded with a derivative such as sugar is used as a carrier, the retention time of the chromatography becomes differentiated, thereby allowing resolution. By utilizing this property, direct resolution can be conducted by the high performance liquid chromatography using a chiral column. Chiral column include, for example, CHIRALPAK AD-H, CHIRALCEL OJ-RH (DAICEL), etc. In the case of an atropisomeric mixture, a standard silica gel column may also be used.

In a case where the atropisomer of the present invention is used as a medicament, the atropisomer of the compound having the aforementioned general formula (I) can be administered as itself (or a composition enriched in that atropisomer), or it (or a compound/composition enriched in it) can be mixed with an appropriate excipient, diluent and the like that are pharmacologically acceptable, and administered orally as a tablet, a capsule, granules, powders, syrup and the like, or be administered parenterally as injection, suppository, adhesive preparation or external preparation.

These pharmaceutical drugs are produced through known methods by using additives such as excipients, lubricants, binders, disintegrants, emulsifiers, stabilizers, correctives and diluents.

The present invention also comprises methods of inhibiting mineralocorticoid receptor activity, both in vitro and in vivo, the method comprising contacting the mineralocorticoid receptor with an effective inhibiting amount of compound of the invention. In one preferred embodiment, the receptor is in a cell. Preferably, the cell is within an animal body, preferably a human body. Such methods are useful, irrespective of any therapeutic effect, to study the role of the mineralocorticoid receptor in biological processes in vitro and in vivo.

The present invention also comprises a method of preventing or treating a mineralocorticoid receptor mediated condition or disease. Such conditions or diseases including, for, example, hypertension, angina pectoris, acute coronary syndrome, congestive heart failure, nephropathy, including diabetic nephropathy, arteriosclerosis, cerebral infarction, fibrosis, primary aldosteronism and edema. The methods of prevention and/or treatment comprise administering to the animal (preferably human) an effective amount of a compound of the invention (alone or in a pharmaceutical composition). As used herein, "treatment" encompasses both curative as well as palliative Although its dosage amount varies depending on the symptom, age and the like, the dose in the case of oral administration for a human adult is from 0.02 mg/kg (preferably 0.1 mg/kg) per dosage as a lower limit to 100 mg/kg (preferably 10 mg/kg) per dosage as an upper limit, and the dose in the case of parental administration is from 0.002 mg/kg (preferably 0.01 mg/kg) per dosage as a lower limit to 10 mg/kg (preferably 1 mg/kg) per dosage as an upper limit, and the dosage can be administered from one to six times per day depending on the symptoms.

The atropisomer of the compounds of the invention having preferred pharmacological and/or pharmacokinetic activity can be routinely determined and identified using the methods described herein and/or known to those skilled in the art.

All publications (patent and non-patent) referenced herein are hereby incorporated by reference.

EXAMPLES

Hereinafter, the present invention will be specifically explained with reference to Examples and Test Examples, however, the present invention is by no means limited to these.

Here, the symbols "NMR" and "MS" in the Examples respectively mean "nuclear magnetic resonance" and "mass spectroscopy". The ratio of solvent for elution described in the portion of separation and purification using chromatography refers to volume ratio, unless otherwise noted. "NMR" means $^1$H-NMR unless otherwise noted, content of the parenthesis shows the solvent for measurement, and TMS (tetramethylsilane) was used as internal standard for all cases. Further, "Anal. Calcd for RATIONAL FORMULA" and "required" respectively means a calculated value for elemental analysis and high resolution mass spectroscopy (HRMS), and the measured value are provided following "found". In addition, in high performance liquid chromatography, analysis and purification were carried out by using the following conditions.

Analytical HPLC
Instrument: SHIMADZU CLASS-VP system (LC-10ADVP/SCL-10AVP/SPD-M10AVP/CTO10ACVP/DGU12A);
oven: 40° C., flow rate: 1.0 mL/min, detection: UV (254 nm).
Preparative HPLC
Instrument: SHIMADZU CLASS-VP system (LC-8A/SCL-10AVP/SIL-10AP/SPD-10AVP/FRC-10A);
oven: rt, flow rate: 20 mL/min, detection: UV (254 nm).

Example 1

1-[(1R,2S)-2-Hydroxy-1-methylpropyl]-4-methyl-N-[4-(methylsulfonyl)phenyl]-5-[2-(trifluoromethyl)phenyl]-1H-pyrrole-3-carboxamide

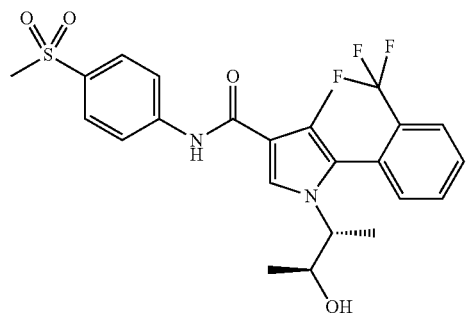 [SMILES: Cc1c(C(=O)Nc2ccc(S(C)(=O)=O)cc2)cn([C@H](C)[C@H](C)O)c1-c1ccccc1C(F)(F)F]

To a solution of 4-methyl-N-[4-(methylsulfonyl)phenyl]-5-[2-(trifluoromethyl)phenyl]-1H-pyrrole-3-carboxamide (28 g, 66 mmol) in anhydrous N,N-dimethylacetamide (DMA) (0.53 L) was added sodium tert-butoxide (15 g, 15 mmol) and stirred at room temperature for 30 min under N$_2$. (4S,5S)-4,5-dimethyl-1,3,2-dioxathiolane 2,2-dioxide (15 g, 99 mmol) in anhydrous DMA (2.0 ml) was added to the solution and stirred at 70° C. for 2.0 h. The reaction mixture was cooled to room temperature and added 2N HCl (0.14 L) and concentrated on a rotary evaporator. To this residue was added anhydrous tetrahydrofuran (THF) (140 ml) and 5N HCl (0.14 L) and stirred at 60° C. for 90 min. The mixture was diluted with ethyl acetate and washed with water, saturated NaHCO$_3$ and brine, then dried over sodium sulfate and concentrated on a rotary evaporator. The resulting residue was purified by silica-gel column chromatography (9:1 to 1:1 dichloromethane:ethyl acetate) to give an atropisomeric mixture of title compound as a white solid (22.5 g, 69%).

$^1$H-NMR (500 MHz, CDCl$_3$) δ: 7.92-7.87 (2H, m), 7.86-7.75 (3.5H, m), 7.72 (1H, s), 7.68-7.56 (2H, m), 7.47 (0.5H, s), 7.38-7.29 (1H, m), 4.09-4.01 (0.5H, m), 3.85-3.75 (0.5H, m), 3.59-3.42 (1H, m), 3.05 (3H, s), 2.07 (3H, s), 1.75-1.61 (1H, m), 1.42 (1.5H, d, J=6.8 Hz), 1.34 (1.5H, d, J=6.8 Hz), 1.11 (1.5H, d, J=6.4 Hz), 1.03 (1.5H, d, J=6.4 Hz);

MS (ESI) m/z: 495 [M+H]$^+$.

Retention time: 5.8 min (isomer A), 7.0 min (isomer B)

chiral HPLC condition: AD-H (0.46 cm×25 cm)

eluent: hexane-EtOH [70:30 (v/v), isocratic]

The atropisomeric mixture of the title compound (5.10 g, 10.3 mmol) was separated by silica-gel column chromatography (1:1 to 1:9 hexane:ethyl acetate) to give one of the atropisomers (isomer A, 900 mg, 1.82 mmol) as a white solid.

Example 1

Isomer A $^1$H-NMR (500 MHz, CDCl$_3$) δ: 7.91 (2H, d, J=8.8 Hz), 7.85-7.80 (3H, m), 7.73 (1H, s), 7.68-7.58 (2H, m), 7.46 (1H, s), 7.35 (1H, d, J=6.8 Hz), 3.85-3.75 (1H, m), 3.58-3.50 (1H, m), 3.06 (3H, s), 2.07 (3H, s), 1.58-1.50 (1H, m), 1.42 (3H, d, J=6.8 Hz), 1.03 (3H, d, J=6.4 Hz).

MS (ESI) m/z: 495 [M+H]$^+$

HRMS (ESI) calcd for C24H26F$_3$N$_2$O$_4$S [M+H]$^+$, required m/z 495.1565, found 495.1570.

Retention time: 5.8 min chiral HPLC condition: AD-H (0.46 cm×25 cm)

eluent: hexane-EtOH [70:30 (v/v), isocratic]

An atropisomer of the title compound (1.0 g, 1.9 mmol) was separated by silica-gel column chromatography (1:1 to 1:9 hexane:ethyl acetate) to give another isomer (isomer B, 0.26 g, 0.50 mmol) as a white solid.

Example 1

Isomer B $^1$H-NMR (500 MHz, CDCl$_3$) δ: 7.90 (2H, d, J=8.3 Hz), 7.84-7.80 (3H, m), 7.78 (1H, s), 7.72 (1H, s), 7.68-7.57 (2H, m), 7.31 (1H, d, J=7.3 Hz), 4.09-4.00 (1H, m), 3.54-3.44 (1H, m), 3.05 (3H, s), 2.07 (3H, s), 1.71 (1H, d, J=4.9 Hz), 1.33 (3H, d, J=6.8 Hz), 1.11 (3H, d, J=6.4 Hz).

MS (ESI) m/z: 495 [M+H]+

HRMS (ESI) calcd for C24H26F$_3$N$_2$O$_4$S [M+H]$^+$, required m/z 495.1565, found 495.1556.

Retention time: 7.0 min chiral HPLC condition: AD-H (0.46 cm×25 cm)

eluent: hexane-EtOH [70:30 (v/v), isocratic]

Example 2

5-[4-Fluoro-2-(trifluoromethyl)phenyl]-1-[(1R,2S)-2-hydroxy-1-methylpropyl]-4-methyl-N-[4-(methylsulfonyl)phenyl]-1H-pyrrole-3-carboxamide Preparation of methyl 5-[4-fluoro-2-(trifluoromethyl)phenyl]-4-methyl-1H-pyrrole-3-carboxylate

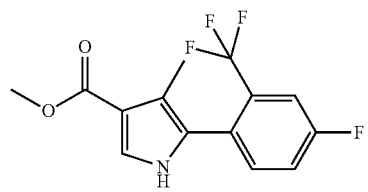 [SMILES: COC(=O)c1c[nH]c(-c2ccc(F)cc2C(F)(F)F)c1C]

A mixture of methyl 5-bromo-4-methyl-1H-pyrrole-3-carboxylate (0.27 g, 1.2 mmol), [4-fluoro-2-(trifluoromethyl)phenyl]boronic acid (0.61 g, 2.9 mmol), Na$_2$CO$_3$ (0.6 g, 5.7 mmol) and palladium tetrakis(triphenylphosphine) (96 mg, 0.083 mmol) in toluene/water (10:1, 10 ml) was stirred at 110° C. for 1.5 h under N$_2$. The reaction mixture was cooled to room temperature and diluted with ethyl acetate. The mixture was washed with water and brine, then dried over sodium sulfate and concentrated on a rotary evaporator. The resulting residue was purified by silica-gel column chromatography (3:1 to 1:3 hexane:ethyl acetate) to give the title compound (0.23 mg, 62%) as a pale yellow solid.

$^1$H-NMR (400 MHz, CDCl$_3$) δ: 8.35-8.25 (1H, brs), 7.48 (1H, dd, J=2.7, 9.0 Hz), 7.45 (1H, d, J=3.1 Hz), 7.40 (1H, dd, J=5.5, 8.2 Hz), 7.30 (1H, dt, J=2.7, 8.2 Hz), 3.82 (3H, s), 2.15 (3H, s).

Preparation of 5-[4-fluoro-2-(trifluoromethyl)phenyl]-4-methyl-1H-pyrrole-3-carboxylic acid

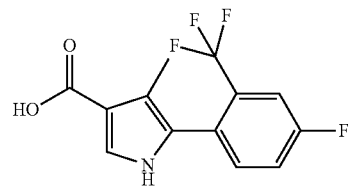 [SMILES: Cc1c(C(=O)O)c[nH]c1-c1ccc(F)cc1C(F)(F)F]

To a solution of methyl 5-[4-fluoro-2-(trifluoromethyl)phenyl]-4-methyl-1H-pyrrole-3-carboxylate (0.23 g, 0.77 mmol) in methanol (4.0 ml) was added 5N NaOH (3.0 ml) and the mixture was stirred at 80° C. for 2.0 h. The reaction mixture was cooled to room temperature and added 2N HCl (8.0 ml). The mixture was diluted with ethyl acetate and washed with water and brine, then dried over sodium sulfate and concentrated on a rotary evaporator. The resulting residue was purified by silica-gel column chromatography (1:1 to 1:9 hexane:ethyl acetate) to give the title compound (211 mg, 96%) as a white solid.

$^1$H-NMR (400 MHz, DMSO-d$_6$) δ: 11.62 (1H, s), 11.34 (1H, s), 7.74 (1H, dd, J=2.5, 9.2 Hz), 7.59 (1H, dt, J=2.5, 8.6 Hz), 7.48 (1H, dd, J=5.8, 8.6 Hz), 7.32 (1H, d, J=3.1 Hz), 1.93 (3H, s).

Preparation of 5-[4-fluoro-2-(trifluoromethyl)phenyl]-4-methyl-N-[4-(methylsulfonyl)phenyl]-1H-pyrrole-3-carboxamide

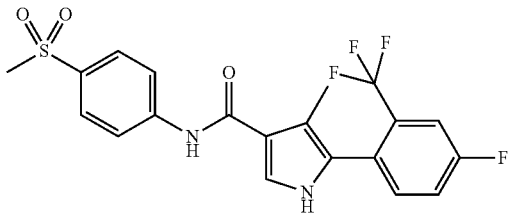 [SMILES: Cc1c(C(=O)Nc2ccc(S(C)(=O)=O)cc2)c[nH]c1-c1ccc(F)cc1C(F)(F)F]

To a suspension of 5-[4-fluoro-2-(trifluoromethyl)phenyl]-4-methyl-1H-pyrrole-3-carboxylic acid (7.7 g, 27 mmol) in dichloromethane (60 ml) was added oxalyl chloride (5.1 ml, 59 mmol). The mixture was stirred at room temperature for 2.0 h, after which time the solvent was removed on a rotary evaporator. To this brown residue was added 4-(methanesulfonyl)aniline hydrochloride (5.8 g, 28 mmol), tetrahydrofuran (THF) (80 ml) and diisopropylethylamine (DIEA) (14 ml, 80 mmol). The solution was stirred at room temperature for 2.0 h. The reaction mixture was concentrated and to the residue was added 2N HCl (80 ml) and water (80 ml) and resulting suspension was stirred for 30 min. The solid was filtered and washed with water and diisopropyl ether (IPE) to give the title compound as a white solid (11 g, 90%).
$^1$H-NMR (500 MHz, DMSO-d$_6$) δ: 11.40 (1H, s), 9.93 (1H, s), 7.98 (2H, d, J=8.3 Hz), 7.84 (2H, d, J=8.3 Hz), 7.77 (1H, d, J=9.3 Hz), 7.68 (1H, s), 7.65-7.57 (1H, m), 7.54-7.47 (1H, m), 3.16 (3H, s), 2.00 (3H, s.

5-[4-Fluoro-2-(trifluoromethyl)phenyl]-1-[(1R,2S)-2-hydroxy-1-methylpropyl]-4-methyl-N-[4-(methylsulfonyl)phenyl]-1H-pyrrole-3-carboxamide

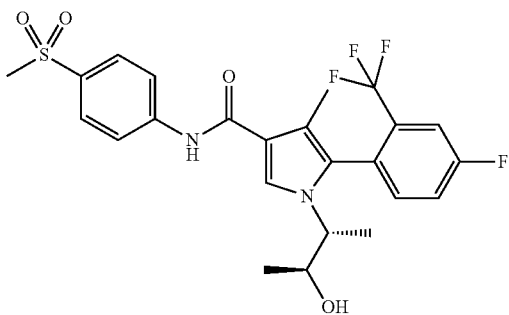 [SMILES: Cc1c(C(=O)Nc2ccc(S(C)(=O)=O)cc2)cn([C@H](C)[C@H](C)O)c1-c1ccc(F)cc1C(F)(F)F]

To a solution of 5-[4-fluoro-2-(trifluoromethyl)phenyl]-4-methyl-N-[4-(methylsulfonyl)phenyl]-1H-pyrrole-3-carboxamide (23 g, 52 mmol) in anhydrous DMA (160 ml) was added sodium tert-butoxide (12 g, 0.12 mol) and stirred at room temperature for 30 min under N$_2$. (4S,5S)-4,5-dimethyl-1,3,2-dioxathiolane 2,2-dioxide (12 g, 78 mmol) in anhydrous DMA (20 ml) was added to the solution and stirred at 70° C. for 2.0 h. The reaction mixture was cooled to room temperature and added 2N HCl (80 ml) and concentrated on a rotary evaporator. To this residue was added anhydrous THF (0.12 L) and 5N HCl (0.14 L) and stirred at 60° C. for 80 min. The mixture was diluted with ethyl acetate and washed with water, satd NaHCO$_3$ and brine, then dried over sodium sulfate and concentrated on a rotary evaporator. The resulting residue was purified by silica-gel column chromatography (1:2, dichloromethane:ethyl acetate) to give an atropisomeric mixture of the title compound (14.3 g, 52%) as a pale yellow solid.
MS (ESI) m/z: 513 [M+H]$^+$.
Retention time: 5.5 min (isomer A), 8.3 min (isomer B)
chiral HPLC condition: AD-H (0.46 cm×25 cm)
eluent: hexane-EtOH [70:30 (v/v), isocratic]
After the racemic mixture of the title compound was synthesized from the same starting material (0.5 g, 1.1 mmol) in a manner similar to that described above, the resulting residue after extraction was purified by silica-gel column chromatography (3:7 to 2:8 hexane:ethyl acetate) to give the atropisomers isomer A (91 mg, 0.18 mmol) and isomer B (62 mg, 0.12 mmol), respectively.

Example 2

Isomer A $^1$H-NMR (400 MHz, CDCl$_3$) δ: 7.87 (2H, d, J=9.0 Hz), 7.85-7.77 (3H, m), 7.53 (1H, d, J=8.6 Hz), 7.48 (1H, s), 7.37-7.33 (2H, m), 3.84-3.74 (1H, m), 3.57-3.48 (1H, m), 3.05 (3H, s), 2.06 (3H, s), 1.70 (1H, d, J=4.7 Hz), 1.41 (3H, d, J=6.7 Hz), 1.04 (3H, d, J=6.7 Hz).
MS (ESI) m/z: 513 [M+H]$^+$
HRMS (ESI) calcd for C24H$_{25}$F$_4$N$_2$O$_4$S [M+H]$^+$, required m/z 513.1471, found 513.1482.
Retention time: 5.5 min
chiral HPLC condition: AD-H (0.46 cm×25 cm)
eluent: hexane-EtOH [70:30 (v/v), isocratic]

Example 2

Isomer B $^1$H-NMR (500 MHz, CDCl$_3$) δ: 7.89 (2H, d, J=8.8 Hz), 7.82 (2H, d, J=8.8 Hz), 7.78 (1H, s), 7.73 (1H, s), 7.53 (1H, dd, J=3.0, 8.3 Hz), 7.39-7.23 (2H, m), 4.10-4.00 (1H, m), 3.50-3.40 (1H, m), 3.05 (3H, s), 2.05 (3H, s), 1.73 (1H, d, J=5.4 Hz), 1.33 (3H, d, J=6.8 Hz), 1.13 (3H, d, J=6.8 Hz).
MS (ESI) m/z: 513 [M+H]$^+$
HRMS (ESI) calcd for C24H$_{25}$F$_4$N$_2$O$_4$S [M+H]$^+$, required m/z 513.1471, found 513.1466.
Retention time: 8.3 min
chiral HPLC condition: AD-H (0.46 cm×25 cm)
eluent: hexane-EtOH [70:30 (v/v), isocratic]

Example 3

5-[4-Chloro-2-(trifluoromethyl)phenyl]-1-[(1R,2S)-2-hydroxy-1-methylpropyl]-4-methyl-N-[4-(methylsulfonyl)phenyl]-1H-pyrrole-3-carboxamide Preparation of methyl 5-[4-chloro-2-(trifluoromethyl)phenyl]-4-methyl-1H-pyrrole-3-carboxylate

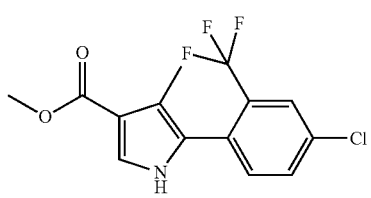 [SMILES: COC(=O)c1c[nH]c(-c2ccc(Cl)cc2C(F)(F)F)c1C]

A mixture of methyl 5-bromo-4-methyl-1H-pyrrole-3-carboxylate (0.44 g, 2.0 mmol), [4-chloro-2-(trifluoromethyl)phenyl]boronic acid (0.90 g, 4.0 mmol), Na$_2$CO$_3$ (0.64 g, 6.0 mmol) and palladium tetrakis(triphenylphosphine) (0.12 g, 0.10 mmol) in toluene/water (9:1, 10 ml) was stirred at 110° C. for 2.0 h under N$_2$. The reaction mixture was cooled to room temperature and diluted with ethyl acetate. The mixture was washed with water and brine, then dried over sodium sulfate and concentrated on a rotary evaporator. The resulting residue was purified by silica-gel column chromatography (dichloromethane) to give the title compound (0.41 g, 65%) as a pale yellow solid.

MS (ES) m/z: 318 [M+H]$^+$

Preparation of 5-[4-chloro-2-(trifluoromethyl)phenyl]-4-methyl-1H-pyrrole-3-carboxylic acid

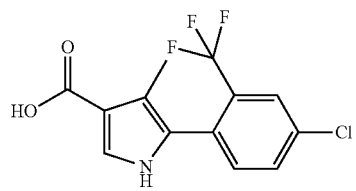 [SMILES: Cc1c(C(=O)O)c[nH]c1-c1ccc(Cl)cc1C(F)(F)F]

To a solution of methyl 5-[4-chloro-2-(trifluoromethyl)phenyl]-4-methyl-1H-pyrrole-3-carboxylate (0.39 g, 1.3 mmol) in methanol (5.0 ml) was added 5N NaOH (5.0 ml) and the mixture was stirred at 80° C. for 3.0 h. The reaction mixture was cooled to room temperature and added formic acid (3.0 ml). The mixture was concentrated on a rotary evaporator. To the residue was added water and triturated. The solid was filtered and dried to give the title compound (0.37 g, 93%) as a brown solid.

$^1$H-NMR (400 MHz, DMSO-d$_6$) δ: 8.38 (1H, s), 7.77 (1H, s), 7.66-7.54 (2H, m), 7.38 (1H, d, J=8.2 Hz), 2.19 (3H, s).

Preparation of 5-[4-chloro-2-(trifluoromethyl)phenyl]-4-methyl-N-[4-(methylsulfonyl)phenyl]-1H-pyrrole-3-carboxamide

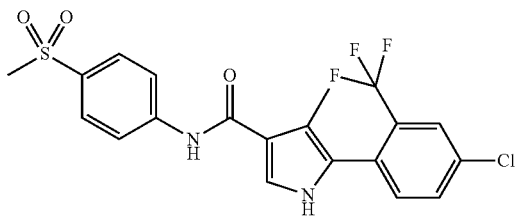 [SMILES: Cc1c(C(=O)Nc2ccc(S(C)(=O)=O)cc2)c[nH]c1-c1ccc(Cl)cc1C(F)(F)F]

To a suspension of 5-[4-chloro-2-(trifluoromethyl)phenyl]-4-methyl-1H-pyrrole-3-carboxylic acid (0.36 g, 1.2 mmol) in dichloromethane (5.0 ml) was added oxalyl chloride (0.3 ml, 3.5 mmol). The mixture was stirred at room temperature for 1.0 h, after which time the solvent was removed on a rotary evaporator. To this brown residue was added THF (5.0 ml), 4-(methanesulfonyl)aniline hydrochloride (0.3 g, 1.4 mmol), and DIEA (0.81 ml, 4.8 mmol). The solution was stirred at room temperature for 3.0 h. The reaction mixture was diluted with ethyl acetate and washed with water and brine, then dried over sodium sulfate and concentrated on a rotary evaporator. To the residue was added IPE and triturated. The solid was filtered to give the title compound (0.24 g, 44%).

$^1$H-NMR (400 MHz, DMSO-d$_6$) δ: 11.39 (1H, s), 9.92 (1H, s), 7.97 (2H, d, J=9.0 Hz), 7.96 (1H, s), 7.87-7.79 (3H, m), 7.69 (1H, d, J=3.1 Hz), 7.47 (1H, d, J=8.2 Hz), 3.15 (3H, s), 2.01 (3H, s).

5-[4-Chloro-2-(trifluoromethyl)phenyl]-1-[(1R,2S)-2-hydroxy-1-methylpropyl]-4-methyl-N-[4-(methylsulfonyl)phenyl]-1H-pyrrole-3-carboxamide

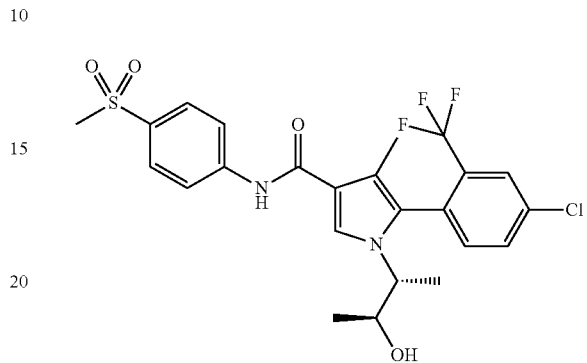

To a solution of 5-[4-chloro-2-(trifluoromethyl)phenyl]-4-methyl-N-[4-(methylsulfonyl)phenyl]-1H-pyrrole-3-carboxamide (21 g, 47 mmol) in anhydrous DMA (234 ml) was added sodium tert-butoxide (10 g, 0.11 mol) and stirred at room temperature for 30 min under N$_2$. (4S,5S)-4,5-dimethyl-1,3,2-dioxathiolane 2,2-dioxide (11 g, 70 mmol) in anhydrous DMA (50 ml) was added to the solution and stirred at 70° C. for 2.0 h. The reaction mixture was cooled to 0° C. and added 2N HCl (100 ml) and concentrated on a rotary evaporator. To this residue was added anhydrous THF (120 ml) and 5N HCl (120 ml) and stirred at 60° C. for 90 min. The mixture was diluted with ethyl acetate and washed with water, satd NaHCO$_3$ and brine, then dried over sodium sulfate and concentrated on a rotary evaporator. The resulting residue was purified by silica-gel column chromatography (1:1 to 1:9 hexane:ethyl acetate) to give an atropisomeric mixture of the title compound (10.9 g, 44%) as a white solid.

$^1$H-NMR (400 MHz, CDCl$_3$) δ: 7.94-7.86 (2H, m), 7.85-7.79 (3H, m), 7.76 (1H, s), 7.73 (0.5H, s), 7.66-7.60 (1H, m), 7.47 (0.5H, s), 7.34-7.24 (1H, m), 4.10-4.00 (0.5H, m), 3.83-3.73 (0.5H, m), 3.58-3.42 (1H, m), 3.05 (3H, s), 2.07 (3H, s), 1.74-1.58 (1H, m), 1.42 (1.5H, d, J=7.0 Hz), 1.33 (1.5H, d, J=7.0 Hz), 1.13 (1.5H, d, J=6.7 Hz), 1.04 (1.5H, d, J=6.7 Hz).

MS (ESI) m/z: 529 [M+H]$^+$

Retention time: 5.1 min (isomer A), 5.7 min (isomer B)

chiral HPLC condition: AD-H (0.46 cm×25 cm)

eluent: hexane-EtOH [70:30 (v/v), isocratic]

The atropisomeric mixture obtained above was separated by silica-gel column chromatography (1:1 to 1:9 hexane:ethyl acetate) to give isomer A and isomer B.

Example 3

Isomer A $^1$H-NMR (400 MHz, CDCl$_3$) δ: 7.91 (2H, d, J=8.6 Hz), 7.84-7.79 (3H, m), 7.70 (1H, s), 7.62 (1H, dd, J=2.4, 8.2 Hz), 7.45 (1H, s), 7.31 (1H, d, J=8.2 Hz), 3.83-3.75 (1H, m), 3.57-3.49 (1H, m), 3.05 (3H, s), 2.07 (3H, s), 1.51 (1H, d, J=2.4 Hz), 1.42 (3H, d, J=7.0 Hz), 1.04 (3H, d, J=6.3 Hz).

MS (ESI) m/z: 529 [M+H]$^+$

HRMS (ESI) calcd for C24H$_{25}$ClF$_3$N$_2$O$_4$S [M+H]$^+$, required m/z 529.1176, found 529.1192.

Retention time: 5.1 min
chiral HPLC condition: AD-H (0.46 cm×25 cm)
eluent: hexane-EtOH [70:30 (v/v), isocratic]

Example 3

Isomer B

¹H-NMR (500 MHz, DMSO-d₆) δ: 9.93 (1H, s), 8.02-7.94 (4H, m), 7.89-7.82 (3H, m), 7.48 (1H, d, J=7.8 Hz), 5.05 (1H, d, J=5.9 Hz), 3.86-3.76 (1H, m), 3.35-3.27 (1H, m), 3.17 (3H, s), 1.92 (3H, s), 1.31 (3H, d, J=6.8 Hz), 0.92 (3H, d, J=6.4 Hz).
MS (ESI) m/z: 529 [M+H]⁺
HRMS (ESI) calcd for $C_{24}H_{25}ClF_3N_2O_4S$ [M+H]⁺, required m/z 529.1176, found 529.1179.
Retention time: 5.7 min
chiral HPLC condition: AD-H (0.46 cm×25 cm)
eluent: hexane-EtOH [70:30 (v/v), isocratic]

Example 4

5-(2-Chloro-4-fluorophenyl)-1-[(1R,2S)-2-hydroxy-1-methylpropyl]-4-methyl-N-[4-(methylsulfonyl)phenyl]-1H-pyrrole-3-carboxamide Preparation of methyl 5-(2-chloro-4-fluorophenyl)-4-methyl-1H-pyrrole-3-carboxylate

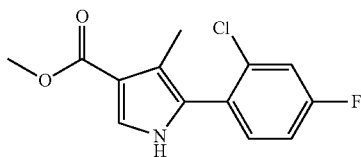 [SMILES: COC(=O)c1c[nH]c(-c2ccc(F)cc2Cl)c1C]

A mixture of methyl 5-bromo-4-methyl-1H-pyrrole-3-carboxylate (0.63 g, 2.8 mmol), (2-chloro-4-fluorophenyl)boronic acid (1.0 g, 5.7 mmol), Na₂CO₃ (0.91 g, 8.6 mmol) and palladium tetrakis(triphenylphosphine) (0.17 g, 0.14 mmol) in toluene/water (10:1, 25 ml) was stirred at 110° C. for 9.0 h under N₂. The reaction mixture was cooled to room temperature and diluted with ethyl acetate. The mixture was washed with water and brine, then dried over sodium sulfate and concentrated on a rotary evaporator. The resulting residue was purified by silica-gel column chromatography (6:1 to 1:1 hexane:ethyl acetate) to give the title compound (634 mg, 84%) as a white solid.
¹H-NMR (400 MHz, CDCl₃) δ: 8.50-8.20 (1H, brs), 7.48 (1H, d, J=3.1 Hz), 7.33 (1H, dd, J=6.3, 8.6 Hz), 7.24 (1H, dd, J=2.7, 8.2 Hz), 7.06 (1H, dt, J=2.7, 8.2 Hz), 3.82 (3H, s), 1.57 (3H, s).

Preparation of 5-(2-chloro-4-fluorophenyl)-4-methyl-1H-pyrrole-3-carboxylic acid

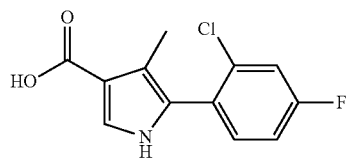

To a solution of methyl 5-(2-chloro-4-fluorophenyl)-4-methyl-1H-pyrrole-3-carboxylate (0.64 g, 2.4 mmol) in methanol (10 ml) was added 5N NaOH (10 ml) and the mixture was stirred at 80° C. for 4.0 h. The reaction mixture was concentrated on a rotary evaporator. To the residue was added water and washed with Et₂O. The resulting solution was neutralized with conc HCl and extracted with ethyl acetate. The organic layer was washed with water and brine, then dried over sodium sulfate and concentrated on a rotary evaporator to give the title compound (610 mg, quant) as a brown solid.
¹H-NMR (400 MHz, DMSO-d₆) δ: 11.67 (1H, s), 11.43 (1H, s), 7.57 (1H, dd, J=2.7, 9.0 Hz), 7.43 (1H, dd, J=6.3, 8.6 Hz), 7.38 (1H, d, J=3.1 Hz), 7.31 (1H, dt, J=2.7, 8.6 Hz), 2.05 (3H, s).

Preparation of 5-(2-chloro-4-fluorophenyl)-4-methyl-N-[4-(methylsulfonyl)phenyl]-1H-pyrrole-3-carboxamide

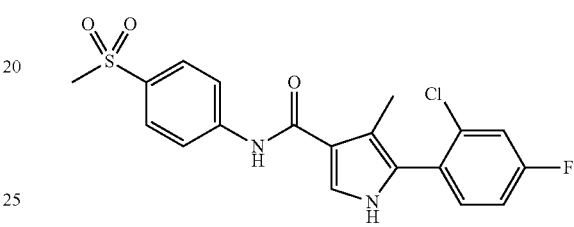

To a suspension of 5-(2-chloro-4-fluorophenyl)-4-methyl-1H-pyrrole-3-carboxylic acid (0.61 g, 2.4 mmol) in dichloromethane (30 ml) was added oxalyl chloride (0.41 ml, 4.8 mmol). The mixture was stirred at room temperature for 2.0 h, after which time the solvent was removed on a rotary evaporator. To this brown residue was added THF (40 ml), 4-(methanesulfonyl)aniline hydrochloride (495 mg, 2.38 mmol), and DIEA (1.6 ml, 9.5 mmol). The solution was stirred at room temperature for 20 h. The reaction mixture was concentrated on a rotary evaporator and 2N HCl (30 ml) was added to the residue. The solid was filtered and washed with 2N HCl, water and IPE to give the title compound (812 mg, 84%) as a brown solid.
¹H-NMR (400 MHz, DMSO-d₆) δ: 11.49 (1H, s), 9.94 (1H, s), 8.00 (2H, d, J=9.0 Hz), 7.85 (2H, d, J=9.0 Hz), 7.74 (1H, d, J=3.1 Hz), 7.60 (1H, dd, J=2.7, 9.0 Hz), 7.46 (1H, dd, J=6.3, 8.6 Hz), 7.33 (1H, dt, J=2.7, 8.6 Hz), 3.17 (3H, s), 2.12 (3H, s).

Preparation of 5-(2-chloro-4-fluorophenyl)-1-[(1R,2S)-2-hydroxy-1-methylpropyl]-4-methyl-N-[4-(methylsulfonyl)phenyl]-1H-pyrrole-3-carboxamide

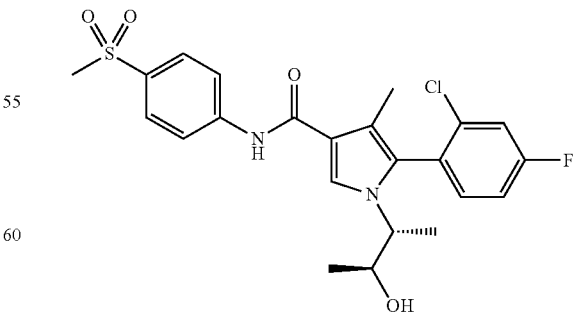

To a solution of 5-(2-chloro-4-fluorophenyl)-4-methyl-N-[4-(methylsulfonyl)phenyl]-1H-pyrrole-3-carboxamide (0.50 g, 1.2 mmol) in anhydrous DMA (8.0 ml) was added sodium tert-butoxide (0.27 g, 2.8 mmol) and stirred at room temperature for 30 min under $N_2$. (4S,5S)-4,5-dimethyl-1,3,2-dioxathiolane 2,2-dioxide (0.28 g, 1.8 mmol) in anhydrous DMA (2.0 ml) was added to the solution and stirred at 70° C. for 2.0 h. The reaction mixture was cooled to room temperature and added 2N HCl (2.0 ml) and concentrated on a rotary evaporator. To this residue was added anhydrous THF (4.0 ml) and 5N HCl (5.0 ml) and stirred at 60° C. for 80 min. The mixture was diluted with ethyl acetate and washed with water, satd $NaHCO_3$ and brine, then dried over sodium sulfate and concentrated on a rotary evaporator. The resulting residue was purified by silica-gel column chromatography (3:7 to 2:8 hexane:ethyl acetate) to give an atropisomeric mixture of the title compound (0.29 g, 50%) as a white solid.

MS (ESI) m/z: 479 [M+H]$^+$

Retention time: 7.0 min (isomer A), 10.4 min (isomer B)

chiral HPLC condition: AD-H (0.46 cm×25 cm)

eluent: hexane-EtOH [70:30 (v/v), isocratic]

The atropisomeric mixture obtained above was separated by chiral HPLC [column: CHIRALPAK AD-H (20 mm×250 mm), eluent: hexane-ethanol (70:30, v/v)] to give isomer A and isomer B.

Example 4

Isomer A $^1$H-NMR (400 MHz, CDCl$_3$) δ: 7.90 (2H, d, J=9.0 Hz), 7.81 (2H, d, J=9.0 Hz), 7.79 (1H, s), 7.47 (1H, s), 7.31-7.25 (2H, m), 7.10 (1H, dt, J=2.7, 8.2 Hz), 3.80-3.70 (1H, m), 3.67-3.57 (1H, m), 3.06 (3H, s), 2.15 (3H, s), 1.59 (1H, d, J=5.1 Hz), 1.52 (3H, d, J=7.0 Hz), 0.98 (3H, d, J=6.3 Hz).

MS (ESI) m/z: 479 [M+H]$^+$

HRMS (ESI) calcd for $C_{23}H_{25}ClFN_2O_4S$ [M+H]$^+$, required m/z 479.1208, found 479.1194

Retention time: 7.0 min chiral HPLC condition: AD-H (0.46 cm×25 cm)

eluent: hexane-EtOH [70:30 (v/v), isocratic]

Example 4

Isomer B $^1$H-NMR (400 MHz, CDCl$_3$) δ: 7.91 (2H, d, J=9.0 Hz), 7.82 (2H, d, J=9.0 Hz), 7.76 (1H, s), 7.55 (1H, s), 7.32-7.21 (2H, m), 7.11 (1H, dt, J=2.7, 8.2 Hz), 4.00-3.89 (1H, m), 3.69-3.60 (1H, m), 3.06 (3H, s), 2.15 (3H, s), 1.58 (1H, d, J=7.4 Hz), 1.43 (3H, d, J=6.7 Hz), 1.06 (3H, d, J=6.3 Hz).

MS (ESI) m/z: 479 [M+H]$^+$

HRMS (ESI) calcd for $C_{23}H_{25}ClFN_2O_4S$ [M+H]$^+$, required m/z 479.1208, found 479.1207

Retention time: 10.4 min chiral HPLC condition: AD-H (0.46 cm×25 cm)

eluent: hexane-EtOH [70:30 (v/v), isocratic].

In the following Test Examples, 1-(2-hydroxyethyl)-4-methyl-N-[4-(methylsulfonyl)phenyl]-5-[2-(trifluoromethyl)phenyl]-1H-pyrrole-3-carboxamide was selected from the compounds described in the prior art (WO 2006/012642) as the most suitable Comparative compound, and was used.

Test Example 1

A plasmid pM-hMR-LBD expressing GAL4-hMR receptor, which has a ligand binding domain (LBD, corresponds to approximately 308 amino acids at the carboxy terminus) of human mineralocorticoid receptor (hMR, NM_000901) bonded to a DNA binding domain of yeast transcription factor GAL4 (corresponding to 147 amino acids at the amino terminus), was prepared. Reporter assay was conducted by using a reporter plasmid (such as STRATAGENE CLONING SYSTEMS, pFR-Luc) including a luciferase gene, having a sequence (UAS sequence) which binds to the DNA binding domain of GAL4.

The plasmid pM-hMR-LBD and the reporter plasmid as obtained above were gene transferred into renal cell line HEK293 of human fetus by lipofection. On the next day, cells were collected by trypsin treatment, and were dispensed with DMEM culture medium containing 5% of FBS treated by activated charcoal, to a white 96-well plate (Costar) with the amount of 95 microliter per well.

The Test Compounds were used by dissolving them in dimethyl sulfoxide at a predetermined concentration, and the test compounds suitably diluted with culture media were added to the cells on the white 96-well plate so that the final concentration becomes 0.1%. When adding the Test Compounds, they were accompanied with 1 nM aldosterone. The well group of Control group 1 was added with dimethyl sulfoxide, and the well group of Control group 2 was added with 1 nM aldosterone. After addition, cultivation was carried out overnight.

On the next day, the culture media was removed, and then luciferase substrate (Wako Pure Chemical Industries, Ltd.) was prepared in accordance with the attached document and were added to each well by 50 microliters. Stirring was conducted for approximately 30 minutes, and the amount of luminescence was measured for each well by using Analyst (Molecular Devices), to obtain luciferase activity. A graph which plots relative luciferase activity values, when the luciferase activity value of Control group 1 was taken as 0% and the luciferase activity value of Control group 2 was taken as 100%, for each of the amount of the test compound addition group was made. From the graph, concentration of the Test Compound which shows the maximum value was calculated as Imax (%), and the concentration which shows Imax/2 was calculated as ICmax50 (nM). ICmax50 values are shown in Table 1.

(Results)

As shown in the following (Table 3), regarding the atropisomers of the present invention, only one of the atropisomers had strong activity, and showed significant mineralocorticoid receptor antagonistic action when compared with the corresponding atropisomeric mixture.

TABLE 3

| Test Compound | ICmax$_{50}$ (nM) | Imax (%) |
|---|---|---|
| Comparative compound | 5.3 | 105 |
| Example 1 | 6.6 | 115 |
| Example 1-isomer A | 2.9 | 117 |
| Example 1-isomer B | >1000 | N.D.[1] |
| Example 2 | 6.2 | 88 |
| Example 2-isomer A | 3.8 | 103 |
| Example 2-isomer B | >1000 | N.D.[1] |
| Example 3 | 6.7 | 95 |
| Example 3-isomer A | 4.6 | 108 |
| Example 3-isomer B | >1000 | N.D.[1] |
| Example 4 | 10 | 106 |
| Example 4-isomer A | 11 | 103 |
| Example 4-isomer B | >1000 | N.D.[1] |

[1] Not determined

Test Example 2

Cynomolgus monkey (male) was used, and was fasted from the day before the administration of the Test Compound.

Administration samples were prepared by adding 0.5% MC (methyl cellulose) solution to the Test Compound, so that the dose becomes 3 mg/2 mL/kg. Each of the administration samples was administered intragastrically to the cynomolgus monkey by using a tube. After the samples were administered, approximately 5 mL of 0.5% MC was administered. For each of the administration samples, a group of two cynomolgus monkeys was administered.

With respect to collection of blood, it was conducted by collecting approximately 0.5 mL of blood from femoral vein using a glass syringe treated with heparin, before administration, and 30 minutes, 1, 2, 4, 6, 8, 24 and 48 hours after administration. Blood was centrifuged (1,700×g, 15 min, 4° C.) to obtain plasma. Plasma was stored in a freezer (−20° C.) until pretreatment.

Preparation of standard solution and internal standard ("IS") solution: Each of the Test Compounds was dissolved in DMSO (dimethyl sulfoxide) to prepare a solution of 10 mM each. Each of the compound solution was diluted with acetonitrile, and thus standard solution was prepared. Further, niflumic acid (Wako Pure Chemical Industries, Ltd.) was dissolved in DMSO at the concentration of 2 mM, followed by dilution with acetonitrile to prepare an IS solution of 2 μM.

Pretreatment of plasma samples: 20 μL of plasma sample was collected, and then 25 μL of purified water, 100 μL of acetonitrile, and 100 μL of methanol was added. For the preparation of a calibration curve, 25 μL of purified water, 20 μL of each of the standard solutions (acetonitrile solution), 80 μL of acetonitrile, and 100 μL of methanol were added to 20 μL of blank plasma. 40 μL of the acetonitrile solution of IS was added to all of the samples, and then the samples were stirred, filtered by suction using Captiva filter plate (Varian, Inc.), and then the filtrate was used as the sample for LC-MS/MS analysis.

Quantitative Determination of Test Compound: Concentration in plasma was analyzed by LC-MS/MS method for each Test Compound.

[HPLC Analysis Conditions]
HPLC: WATERS 2795 (Waters Corporation);
Column: CAPCELL PAK C8, 2.0 mm I.D.×50 mm, 5 μm (Shiseido Co., Ltd.)
Mobile Phase: A=5 mM ammonium acetate aqueous solution, B=acetonitrile
[MS/MS Analysis Conditions]
MS: Quattro micro API (Waters Corporation)
Ionization Method: Electrospray Ionization ("ESI")
Ionization Mode: Positive
Detection Mode: MRM
Analysis: Pharmacokinetic parameter was calculated from concentration of each of the drugs in plasma, by using WinNonlin Professional (Ver. 4.0.1, Pharsight Corporation). Here, noncompartment model was used as the model for parameter calculation.

(Results)

As shown in (Table 4), the result of evaluation of Comparative compound and the Example compounds listed below revealed that the atropisomer described in Test Example 1 having high activity showed considerably improved concentration in plasma when compared with the Comparative compound which is in a racemic form.

TABLE 4

| Test Compound | AUC [1] (μg·h/mL) | Cmax [2] (μg/mL) |
| --- | --- | --- |
| Comparative compound [3] | 4.09 | 0.23 |
| Example 2-isomer A | 30.32 | 1.28 |
| Example 3-isomer A | 42.49 | 1.44 |

[1] AUC: Area under the plasma concentration (measured by LC-MS/MS method) versus time curve;
[2] Cmax: Maximum concentration
[3] three Cynomolgus monkeys were used

INDUSTRIAL APPLICABILITY

Since the atropisomers of a compound represented by the general formula (I) of the present invention shows pharmacological activities such as particularly superior mineralocorticoid receptor antagonistic action, antihypertensive action, vasodilation action, cardioprotective action, nephropathy inhibitory action, antiarteriosclerotic action and diuretic action, and is high in safety, it is useful as a preventive drug or a therapeutic drug for hypertension, angina pectoris, acute coronary syndrome, congestive heart failure, nephropathy, including diabetic nephropathy, arteriosclerosis, cerebral infarction, fibrosis and primary aldosteronism.

We claim:

1. A mineralocorticoid receptor antagonist compound of general formula (I):

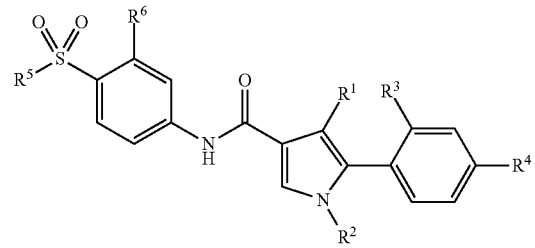

(I)

an N-oxide thereof; a diastereomer, racemate, or compound enriched in a diastereomer thereof; an atropisomer, equal mixture of atropisomers, or compound enriched of an atropisomer thereof; or a pharmaceutically acceptable salt of any of the foregoing, wherein, $R^1$ represents a C1-C3 alkyl group;
$R^2$ represents a 2 hydroxy-1-methylpropyl group;
$R^3$ represents a halogeno group, a C1-C3 alkyl group, a C1-C3 alkoxy group, a halogeno-C1-C3 alkyl group or a halogeno-C1-C3 alkoxy group;
$R^4$ represents a hydrogen atom, a halogeno group or a C1-C3 alkyl group;
$R^5$ represents a C1-C3 alkyl group; and
$R^6$ represents a hydrogen atom, a halogeno group, a C1-C3 alkyl group or a C1-C3 alkoxy group.

2. The compound according to claim 1 which is an atropisomer or pharmaceutically acceptable salt of the atropisomer.

3. The compound according to claim 1, wherein $R^1$ is a methyl group.

4. The compound according to claim 1, wherein $R^2$ is a (1R,2S)-2-hydroxy-1-methylpropyl group.

5. The compound according to claim 1, wherein $R^3$ is a methyl group, a chloro group, a halogenomethyl group or a halogenomethoxy group.

6. The compound according to claim 1, wherein $R^3$ is a chloro group, a difluoromethyl group, a trifluoromethyl group, a difluoromethoxy group or a trifluoromethoxy group.

7. The compound according to claim 1, wherein $R^3$ is a chloro group or a trifluoromethyl group.

8. The compound according to claim 1, wherein $R^4$ is a hydrogen atom or a halogeno group.

9. The compound according to claim 1, wherein $R^4$ is a hydrogen atom, a fluoro group or a chloro group.

10. The compound according to claim 1, wherein $R^5$ is a methyl group.

11. The compound according to claim 1, wherein $R^6$ is a hydrogen atom, a chloro group or a methyl group.

12. The compound according to claim 1, wherein $R^6$ is a hydrogen atom.

13. A compound that is:
1-[2-hydroxy-1-methylpropyl]-4-methyl-N-[4-(methylsulfonyl)phenyl]-5-[2-(trifluoromethyl)phenyl]-1H-pyrrole-3-carboxamide;
5-[4-fluoro-2-(trifluoromethyl)phenyl]-1-[2-hydroxy-1-methylpropyl]-4-methyl-N-[4-(methylsulfonyl)phenyl]-1H-pyrrole-3-carboxamide;
5-[4-chloro-2-(trifluoromethyl)phenyl]-1-[2-hydroxy-1-methylpropyl]-4-methyl-N-[4-(methylsulfonyl)phenyl]-1H-pyrrole-3-carboxamide;
5-(2-chloro-4-fluorophenyl)-1-[2-hydroxy-1-methylpropyl]-4-methyl-N-[4-(methylsulfonyl)phenyl]-1H-pyrrole-3-carboxamide;
an N-oxide thereof; a diastereomer, racemate, or compound enriched in a diastereomer thereof; an atropisomer, equal mixture of atropisomers, or compound enriched of an atropisomer thereof; or a pharmaceutically acceptable salt of any of the foregoing.

14. A compound that is:
1-[(1R,2S)-2-hydroxy-1-methylpropyl]-4-methyl-N-[4-(methylsulfonyl)phenyl]-5-[2-(trifluoromethyl)phenyl]-1H-pyrrole-3-carboxamide;
5-[4-fluoro-2-(trifluoromethyl)phenyl]-1-[(1R,2S)-2-hydroxy-1-methylpropyl]-4-methyl-N-[4-(methylsulfonyl)phenyl]-1H-pyrrole-3-carboxamide;
5-[4-chloro-2-(trifluoromethyl)phenyl]-1-[(1R,2S)-2-hydroxy-1-methylpropyl]-4-methyl-N-[4-(methylsulfonyl)phenyl]-1H-pyrrole-3-carboxamide;
5-(2-chloro-4-fluorophenyl)-1-[(1R,2S)-2-hydroxy-1-methylpropyl]-4-methyl-N-[4-(methylsulfonyl)phenyl]-1H-pyrrole-3-carboxamide;
an N-oxide thereof; a diastereomer, racemate, or compound enriched in a diastereomer thereof; an atropisomer, equal mixture of atropisomers, or compound enriched of an atropisomer thereof; or a pharmaceutically acceptable salt of any of the foregoing.

15. An atropisomer of the compound according to claim 1 which shows stronger mineralocorticoid receptor antagonist activity compared to the other atropisomer(s) of the compound.

16. A pharmaceutical composition comprising the atropisomer according to claim 1 and a pharmacologically acceptable carrier, diluent, or excipient.

17. A pharmaceutical composition comprising a compound according to claim 14 or a pharmaceutical acceptable salt thereof together with a pharmacologically acceptable carrier, diluent, or excipient.

18. An atropisomer of a compound according to claim 14 or pharmaceutically acceptable salt thereof.

19. A pharmaceutical composition comprising an atropisomer according to claim 18 or a pharmaceutical acceptable salt thereof together with a pharmacologically acceptable carrier, diluent, or excipient.

* * * * *